US011432735B2

(12) United States Patent
Vaara et al.

(10) Patent No.: US 11,432,735 B2
(45) Date of Patent: Sep. 6, 2022

(54) RADIOTHERAPY SYSTEM FOR ACCURATE LOCATING OF 3D OBJECTS FROM MAGNETIC RESONANCE IMAGES

(71) Applicant: KONINKLIJKE PHILIPS N.V., Eindhoven (NL)

(72) Inventors: Teuvo Juhani Vaara, Veikkola (FI); Erkki Tapani Vahala, Hyvinkaa (FI)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 16/343,882

(22) PCT Filed: Oct. 19, 2017

(86) PCT No.: PCT/EP2017/076656
§ 371 (c)(1),
(2) Date: Apr. 22, 2019

(87) PCT Pub. No.: WO2018/077705
PCT Pub. Date: May 3, 2018

(65) Prior Publication Data
US 2020/0054234 A1 Feb. 20, 2020

(30) Foreign Application Priority Data
Oct. 25, 2016 (EP) .................................... 16195502

(51) Int. Cl.
*A61B 5/00* (2006.01)
*A61B 5/055* (2006.01)
(Continued)

(52) U.S. Cl.
CPC .............. *A61B 5/055* (2013.01); *A61B 34/10* (2016.02); *A61N 5/1049* (2013.01); *A61N 2005/1055* (2013.01)

(58) Field of Classification Search
None
See application file for complete search history.

(56) References Cited

U.S. PATENT DOCUMENTS

| 9,786,054 B2 | 10/2017 | Taguchi |
| 10,307,616 B2 | 6/2019 | Vahala |
| (Continued) | | |

FOREIGN PATENT DOCUMENTS

JP 200578176 3/2005

OTHER PUBLICATIONS

Makni et al "Combining a Deformable Model and a Probabilistic Framework for an Automatic 3D Segmentation of Protate on MRI" Int. J. Cars (2009) 4 p. 181-188.
(Continued)

*Primary Examiner* — Joel F Brutus (57) ABSTRACT

The present disclosure relates to a method for controlling a magnetic resonance imaging guided radiation therapy apparatus (100) comprising a magnetic resonance imaging system (106). The method comprises: acquiring magnetic resonance data using the magnetic resonance imaging system from an organ (146), the organ being marked by a predefined marker; the magnetic resonance data comprising 3D image data; identifying in a reconstructed 2D image of the magnetic resonance data at least one signal void candidate of the marker; processing the 3D image data and the identified signal void for calculating a likelihood that the identified signal void candidate is part of the marker; outputting an indication of the calculated likelihood; in response to the outputting, receiving a user input specifying performing a radio therapy; and controlling the irradiation of the organ using the radiation therapy.

20 Claims, 2 Drawing Sheets

(51) Int. Cl.
*A61B 34/10* (2016.01)
*A61N 5/10* (2006.01)

(56) References Cited

U.S. PATENT DOCUMENTS

| | | |
|---|---|---|
| 2004/0218797 A1 | 11/2004 | Ladak et al. |
| 2005/0027188 A1 | 2/2005 | Metaxas et al. |
| 2008/0058580 A1* | 3/2008 | Black ................ A61M 37/0069 600/8 |
| 2009/0048515 A1 | 2/2009 | Suri et al. |
| 2009/0285466 A1 | 11/2009 | Hipp et al. |
| 2012/0089008 A1* | 4/2012 | Strehl .................. G01R 33/286 600/411 |
| 2013/0064439 A1 | 3/2013 | Khurd et al. |
| 2013/0116548 A1 | 5/2013 | Kumar et al. |
| 2013/0201893 A1 | 8/2013 | Hu et al. |
| 2014/0016759 A1 | 1/2014 | Ngar et al. |
| 2014/0128883 A1 | 5/2014 | Piron et al. |
| 2014/0275984 A1 | 9/2014 | Hermann et al. |
| 2015/0148660 A1 | 5/2015 | Weiss et al. |
| 2015/0343237 A1 | 12/2015 | Hausotte |
| 2015/0367145 A1 | 12/2015 | Sjolund et al. |
| 2016/0015465 A1 | 1/2016 | Steines et al. |
| 2018/0078787 A1 | 3/2018 | Schadewaldt |
| 2021/0121263 A1 | 4/2021 | Grinstaff |

OTHER PUBLICATIONS

International Search Report dated Jan. 23, 2018.

* cited by examiner

RADIOTHERAPY SYSTEM FOR ACCURATE LOCATING OF 3D OBJECTS FROM MAGNETIC RESONANCE IMAGES

CROSS REFERENCE TO RELATED APPLICATIONS

This application is a U.S. national phase application of International Application No. PCT/EP2017/076656 filed on Oct. 19, 2017, which claims the benefit of EP Application Serial No. 16195502.6 filed on Oct. 25, 2016 and is incorporated herein by reference.

FIELD OF THE INVENTION

The invention relates to energy treating devices, in particular to the use of a therapy system for controlling irradiation of an affected part of an organ being marked by a predefined marker.

BACKGROUND OF THE INVENTION

Radiation therapy (RT) treatment planning systems and image analysis software require tools that help users finding organs in magnetic resonance images. In particular, there is a need to improve the processing of the magnetic resonance (MR) images in MRI-only based RT or MRI-assisted RT of organs such as the prostate.

SUMMARY OF THE INVENTION

Various embodiments provide for a magnetic resonance imaging guided radiation therapy apparatus, an improved method, and a computer program product as described by the subject matter of the independent claims. Advantageous embodiments are described in the dependent claims.

In one aspect, the invention relates to a magnetic resonance image-guided radiation therapy apparatus (MRI apparatus) for controlling irradiation of an affected part of an organ being marked by a predefined marker. The MRI apparatus comprises a magnetic resonance imaging system, a processor for controlling the apparatus; and a memory containing machine executable instructions, wherein execution of the instructions causes the processor to:
  acquire magnetic resonance data using the magnetic resonance imaging system (106) from the organ, the magnetic resonance data comprising 3D image data or 3D image data and 2D image data;
  identify in a reconstructed 2D image reconstructed from the 3D image data or from the 2D image data at least one signal void candidate of the marker;
  process the 3D image data and the identified signal void for calculating a likelihood that the identified signal void candidate is part of the marker;
  output an indication of the calculated likelihood;
  in response to the outputting of the calculated likelihood, receive a user input with respect to a radiation therapy plan; and
  control the irradiation of the organ in accordance with the radiation therapy plan.

For example, a single radiotherapy plan may be used and the calculated likelihood may be used for position verification of the organ. In another example, the calculated likelihood may be used not only for position verification but also for the planning purposes e.g. for correcting the density information in the area of the marker location.

When MRI-based radiation therapy (RT) planning of prostate is prepared in treatment planning system, there is often a need to manually delineate the shape of a small piece of metal wire that has been inserted into prostate. Accurate delineation is necessary for precise alignment of prostate for the RT. The present apparatus and method may enable an accurate delineation of the marker inserted in the organ to be treated.

The present apparatus and method may enable outputs such that the user of the apparatus can locate the known (possibly deformed) shape of a 3D object in the MR image for subsequent marking or contouring of the 3D object. The marker comprises the 3D object. The apparatus may be used not only RT of prostate but can also be used in case of liver or other organs.

The shape of the marker may change over time inside the organ e.g. while treating or irradiating the affected part of the organ. Thus, the initial shape of the marker may not be valid anymore. The present apparatus and method may enable a dynamic processing (e.g. automatic, or periodic or event or user triggered processing) of data in order to dynamically provide an up-to-date shape of the marker.

Another advantage may be that the above features may enable to provide better control of the radiation dose distribution by accurately computing the radiation dose distribution based on an up to date shape of the marker.

Another advantage may be that the present method may save resources and processing time by allowing radiation dose planning on the MR image and thus avoiding a computer tomography (CT) image acquisition and reconstruction. This is in contrast to a conventional method where in addition to a MR procedure a CT based procedure is required for an accurate radiotherapy planning, which is the current standard e.g. for prostate radiation therapy planning.

Another advantage may be that the present method may enable locating the deformed shape of a signal void arising from the shape of the foreign marker in the MR image. This may particularly be advantageous as the detection of the markers in MR images may not be as easier as in CT images because the physical mechanism of image creation is different. Also, with MR imaging, the contrast in a tissue may vary a lot more than in CT images.

The marker may comprise for example an object of a-priori known or predefined dimensions and/or a-priori known or predefined contrast. For example, the marker may be made of metal, or plastic or material mixtures.

The reconstructed 2D image may be reconstructed from 2D or 3D image data. For example, when 3D image data is acquired in slices using a multislice technique, the reconstructed 2D image may be a reconstructed slice of the slices. A user may want to identify the signal void on the reconstructed 2D image and that identified signal void is used to look into image data of consecutive slices to check whether this is a marker, wherein the 3D image data comprises image data of the consecutive slices. In one example, the image data of the reconstructed 2D image and the 3D image data may be registered.

The term "registering" refers to alignment between images of the same or different subjects, acquired using the same or different imaging modalities. Image registration establishes correspondence of spatial information in different images so that corresponding features can be related. Image registration and comparison may be between 2D and 3D image data of the organ (e.g. of a patient or individual).

The term "signal void" refers to a region of the 2D image emitting no radiofrequency signal, generally presented as a dark area in the MR image or emitting signals of a known quality or contrast e.g. caused or originated from liquid filled containers or bags, plastic inserts, or organs. This is because there are no activated protons in the region (such as flowing blood) or because of uncompensated dephasing. The signal void to may refer or comprise one or more pixels or voxels of that region. Signal void may be caused by different sources. For example, signal void may occur at the area that has some minor flow disruption caused by normal anatomical structures, for example, signal flow void is present at the mid ventricular area where the papillary muscle acts as a physiological disruptor. The signal void may occur by the presence of an object such as a metal in the imaged object.

In one example, the outputting and receiving steps may be optional. For example, upon determining the likelihoods, a comparison of the determined likelihoods in association with their signal voids may be performed with predefined reference values of the likelihoods in association with their reference signal voids. Based on the comparison results (e.g. based on the shift of the signal voids and/or likelihoods) a predefined RT plan may be used to control the irradiation of the organ. For example, the initial shape of the marker may be determined on a MR image of the organ, and reference signal voids may be identified on a reference MR image and their likelihoods may be calculated. The reference likelihood values and associated reference signal voids (e.g. pixels of the reference MR image) may be stored. Upon calculating the current likelihoods for currently identified signal voids, the obtained values and position in the current MR image may be compared with stored reference values. (e.g. the reference MR image and the current MR image may be registered before performing the calculation and comparison). Furthermore, radiation therapy plans may be predefined and stored in association with predefined likelihoods and/or signal void values.

The step of identifying or determining signal void candidates may be performed using one or more MR images e.g. the user may identify a void candidate in each slice of multiple slices in order to better delineate the shape of the marker. For each identified void candidate the steps defined above may be performed.

According to one embodiment, execution of the instructions further causes the processor to automatically identify the signal void using magnetic resonance properties of pixels of the 2D image. This may provide a systematic method for checking the shape of the marker. For example, the steps of identifying the signal voids and determining their corresponding likelihoods may be repeated and in each iteration the shape of the marker may be determined. In case, the shape of the marker changes with respect to the previous iteration the following steps of outputting, receiving and controlling the apparatus may be performed.

According to one embodiment, execution of the instructions further causes the processor to display on a graphical user interface the 2D image and to receive a selection of the identified signal void. This may enable a controlled irradiation of the organ.

According to one embodiment, the outputting comprises displaying an indication of the likelihood in association with the 2D image. For example, a pointer may be displayed on top of the signal void in the 2D image. The pointer may have a colour indicating the likelihood e.g. a green colour may indicate that the likelihood is higher than 90%.

According to one embodiment, the processing step comprises: identifying pixels of the 2D image corresponding to the identified signal void, comparing magnetic resonance properties of the pixels with magnetic resonance properties of voxels of the 3D image data; and calculating the likelihood using the comparison result.

A voxel is a volume element, defined in 3D space. Its dimensions may be given by the pixel, together with the thickness of the slice. Slice thicknesses may be achieved using 2D multislice imaging or with 3D scan techniques.

For example, when the user of the therapy apparatus selects a 2D region (e.g. signal void candidate) on the 2D image, the present method may fit one or more a-priori selected models to contain that selected area such as sample brute-force fitting. Examples of such models may include basic models of human organs, typical diseases in a selected body area, or commercially available artificial objects e.g. MRI compatible in-body applicators. The goodness of the fit may be normalized to a user visible range or categories. The fit value may be shown (e.g. in interactive manner) to the user, so that multiple possible sites can be quickly covered and best matches found based on the visual appearance on the 2D image morphology, the fit quality visualization, and the anatomical knowledge the user has of the possible locations of the marker to be located. Once the best locations are found, the user may apply the models or mark the locations. For example, a user may select a single pixel by clicking with a mouse on the 2D MR image. Pixels that surround or relate to the selected pixel in addition to the selected pixel may be grouped to form a group of pixels. In this case, the pixels surroundings may be included in a search (e.g. using visible field-of-view or view port resolution dependant calc. or a pixel window 'within 5 pixels' search criteria to take into account mouse pointing inaccuracies). The method may process each pixel of the group. For each pixel of the group, a pre-calculated array of small 3D matrices containing the model mask and offset of the matrix from the pixel is applied at the pixel location in the 3D image volume (e.g. 3D MR data may be examined, looking for local structures such as edges or regions, which are assembled into matrix in an attempt to identify the object of interest) to calculate correlation. The best correlation may be given as the goodness of the fit.

According to one embodiment, execution of the instructions further causes the processor to: provide reference values of one or more parameters describing the shape of the marker; process the 3D image data for determining the shape of the marker using magnetic resonance properties of the signal void; determining values of the parameters using the determined shape of the marker; comparing the determined values with the reference values; and calculate the likelihood using the comparison result.

Accurate delineation of shapes of markers is time consuming and error prone and may require expertise. This embodiment may use the shape (e.g. length and volume) of the marker, such as a piece of metal wire or other object, as a priori information to help to find the identified signal void of the marker from the MR image. Implementation could be for example such that a predefined shape (of a marker such as Gold Anchor™ wire) is dragged on top of the area where the signal void candidate is and the present method uses the length (and volume) information to limit the search of markers place and shape to the likely nearby image elements in the 3D volume (voxels). Because the marker (e.g. wire) may deform but not shrink or expand, the parameters may be defined using this information for deducing the likely location of the marker. Because MR images typically come from same imaging session, the different contrasts can be easily used because the images are typically adequately co-registered. They can also be re-registered prior to the shape search process. For example, a model that represents the expected shape and local grey-level structure of the marker in the MR image may be used.

The ability to pre-define arbitrary shape of the marker (that is inserted in the organ) and allowing the present method to use that information to limit the search of the marker shape from the image space using this shape information. With the MRI an exploitation of many image contrasts in the search may be used too because the images are coming from same imaging session and thereby readily co-registered.

According to one embodiment, execution of the instructions further causes the processor to repeat the identifying and the processing steps for delineating the shape of the marker on the 2D image. This embodiment may be advantageous as it may enable a controlled selection of the signal voids e.g. the user may provide accurately determined signal voids one by one. This may increase the probability to find the correct shape of the marker.

According to one embodiment, the at least one signal void comprises a plurality of signal voids, wherein the processing of the 3D image data and each identified signal void of the plurality of signal voids is performed for calculating a likelihood that each of the identified signal void candidate is part of (or caused or originated by) the marker; wherein execution of the instructions further causes the processor to build a shape of the marker using the likelihood of the plurality of signal voids. This embodiment may enable a single processing of all identified signal voids which may save resources that would otherwise be required by an individual processing of the signal voids.

According to one embodiment, the parameters are shape independent parameters. For example, the parameter may comprise the volume or length or size of the marker. Because the marker may deform, using parameter that are shape-independent may increase the accuracy of the present method for determining the shape of the marker on the 2D image.

According to one embodiment, the magnetic resonance properties comprising at least one of intensity or magnitude of the signal. The more properties are used the more accurate the shaping of the marker is.

According to one embodiment, the marker is an object having a predefined shape and/or predefined contrast. In one example, the organ is a prostate.

In another example, as method may be provided using prior knowledge about the shape of a structure (e.g. a gold seed or wire). When a user selects a certain area in an image that could potentially be this structure, the system calculates a likelihood that this area is indeed part of the structure selected. Also an algorithm could automatically search in the image for presence of this structure based on its predefined shape.

In a further example, a treatment planning system in which accurate locating and marking (delineation) of 3D objects from MRI images is performed using visual cues is provided. The method of locating the structure of the 3D object may be the method described using likelihood calculation for identified signal voids on the MR images.

In another aspect, the invention relates to a computer program product comprising machine executable instructions for execution by a processor controlling a magnetic resonance imaging guided radiation therapy apparatus, wherein execution of the machine executable instructions causes the processor to:

receive magnetic resonance data, the magnetic resonance data comprising 3D image data or 3D image data and 2D image data that are acquired using a magnetic resonance imaging system from an organ (146), the organ being marked by a predefined marker;

identify in a reconstructed 2D image reconstructed from the 3D image data or from the 2D image data at least one signal void candidate of the marker;

process the 3D image data and the identified signal void for calculating a likelihood that the identified signal void candidate is part of the marker;

output an indication of the calculated likelihood;

in response to the outputting, receive a user input with respect to a radiation therapy plan; and control the irradiation of the organ using the radiation therapy plan.

In another aspect, the invention relates to a method for controlling a magnetic resonance imaging guided radiation therapy apparatus comprising a magnetic resonance imaging system. The method comprises:

acquiring magnetic resonance data using the magnetic resonance imaging system from an organ (146), the organ being marked by a predefined marker; the magnetic resonance data comprising 3D image data or 3D image data and 2D image data;

identifying in a reconstructed 2D image reconstructed from the 3D image data or from the 2D image data at least one signal void candidate of the marker;

processing the 3D image data and the identified signal void for calculating a likelihood that the identified signal void candidate is part of the marker;

outputting an indication of the calculated likelihood;

in response to the outputting of the calculated likelihood, receiving a user input with respect to a radiation therapy plan; and controlling the irradiation of the organ in accordance with the radiation therapy plan.

Magnetic resonance image data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

In the following, like numbered elements in the figs. are either similar elements or perform an equivalent function. Elements which have been discussed previously will not necessarily be discussed in later figs. if the function is equivalent.

Various structures, systems and devices are schematically depicted in the figs. for purposes of explanation only and so as to not obscure the present invention with details that are well known to those skilled in the art. Nevertheless, the attached figs. are included to describe and explain illustrative examples of the disclosed subject matter.

Figure 1:
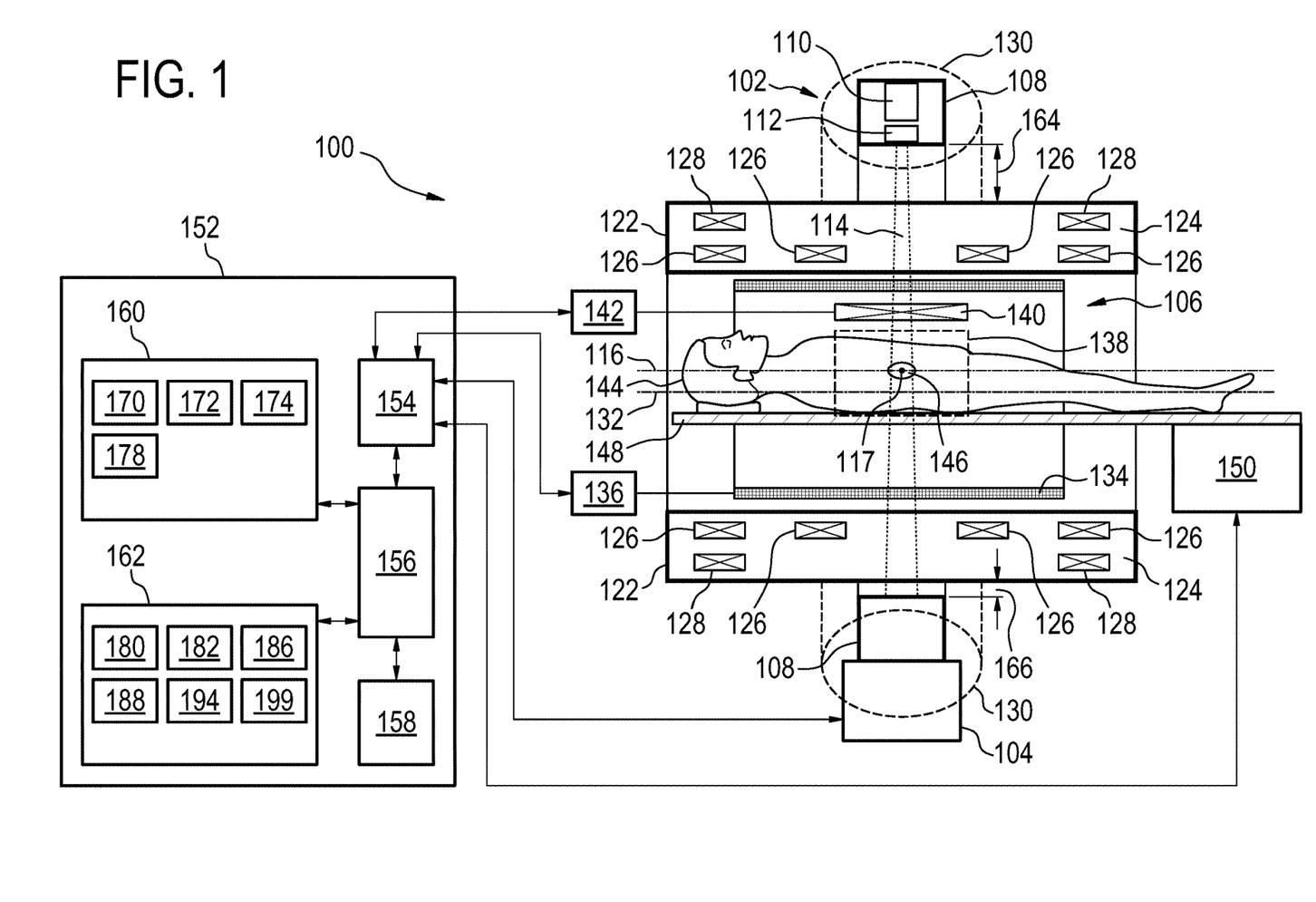
FIG. 1 shows a cross-sectional and functional view of a therapy system.

FIG. 1 shows a cross-sectional and functional view of a therapy system 100. The therapy system 100 is shown as comprising a radiotherapy apparatus 102 and a magnetic resonance imaging module 106. The radiotherapy apparatus 102 comprises a ring mechanism 108. The ring mechanism 108 supports a radiotherapy source 110. The radiotherapy source 110 is representative and may be a LINAC x-ray source, an x-ray 2 and a radioisotope gamma radiation source. Adjacent to the radiotherapy source 110 is a multi-leaf beam collimator 112 for collimating a radiation beam 114 that is generated by the radiotherapy source 110. The ring mechanism 108 is also adapted for moving e.g. rotating the radiotherapy source 110 and the beam collimator 112 about a rotational point 117 of the radiotherapy apparatus 102. A rotational axis 116 passes through the rotational point 117.

The magnetic resonance imaging module 106 is shown as comprising a main magnet 122. The ring mechanism 108 is ring-shaped and surrounds the main magnet 122. The main magnet 122 shown in FIG. 1 is a cylindrical type superconducting magnet. However, other magnets are also applicable for embodiments of the invention. The main magnet 122 has a supercooled cryostat 124. Inside the cryostat 124 there is a collection of superconducting coils 126. There are also compensation coils 128 whose current opposes the direction of current in the superconducting coils 126. This creates a low magnetic field zone 130 that circles or encompasses the main magnet 122. The cylindrical main magnet 122 is shown as having an axis 132 of symmetry.

Within the bore of the magnet there is a magnetic field gradient coil 134 which is used for acquisition of image magnetic resonance data to spatially encode objects within an imaging volume 138 of the main magnet 122. The magnetic field gradient coil 134 is connected to a magnetic field gradient coil power supply 136. The magnetic field gradient coil 134 is intended to be representative. Typically magnetic field gradient coils contain three separate sets of coils for spatially encoding in three orthogonal spatial directions. The imaging volume 138 is located in the center of the main magnet 122.

Adjacent to the imaging volume 138 is a radio frequency (RF) coil 140 for manipulating the orientations of magnetic spins within the imaging volume 138 and for receiving radio transmissions from spins also within the imaging volume 138. The radio frequency coil 140 is connected to a radio frequency transceiver 142. The radio frequency coil 140 and radio frequency transceiver 142 may be replaced by separate transmit and receive coils and a separate transmitter and receiver. It is understood that the radio frequency coil 140 and the radio frequency transceiver 142 are simply representative.

Within the center of the main magnet 122 is also located a subject 144. The subject 144 has a target volume (or target zone) 146 and is shown as reposing on a patient carrier 148. The RF coil 140 may transmit RF pulses into the target volume 146. The patient carrier 148 has a mechanical positioning system 150. The mechanical positioning system 150 is adapted for positioning the patient carrier 148 within the main magnet 122. Depending upon the space available inside of the main magnet 122, the mechanical positioning system 150 may move the patient carrier 148 in different directions including a direction perpendicular to the magnet axis 132. If there is more space available inside the main magnet 122 the mechanical positioning system 150 may have more degrees of freedom. For instance the mechanical positioning system 150 may position the patient carrier 148 with six degrees of freedom.

The radio frequency transceiver 142, the magnetic field gradient coil power supply 136, the mechanical actuator 104, and the mechanical positioning system 150 are all shown as being connected to a hardware interface 154 of a computer system 152. The computer system 152 uses a processor 156 to control the therapy system 100.

The computer system 152 shown in FIG. 1 is representative. Multiple processors and computer systems may be used to represent the functionality illustrated by this single computer system 152. The computer system 152 comprises the hardware interface 154 which allows the processor 156 to send and receive messages to components of the therapy system 100. The processor 156 is also connected to a display device 158, computer storage 160, and computer memory 162. The display device 158 may comprise a touch screen sensitive display device. The display device may be provided with a detachable stylus pen to allow a user to more efficiently manipulate the display device 158.

The radiotherapy apparatus 102 is not shown as being connected to the hardware interface 154. The radiotherapy apparatus 102 may be, for example, connected to the hardware interface 154 and communicates with the computer system 152 via the mechanical actuator 104.

For the example shown in FIG. 1, the rotational axis 116 of the radiotherapy apparatus is not coaxial with the magnet axis 132. The rotational point 117 is shown as being off center from the magnet axis 132. It can be seen that the target zone 146 is off-center and away from the magnet axis 132. The radiotherapy apparatus 102 has been moved by mechanical actuator 104 such that the rotational point 117 of the radiotherapy apparatus is within the target zone 146. It can be seen that the ring mechanism 108 has been moved relative to the magnet 122.

The radiation beam 114 passes through the rotational point 117. Placing the rotational point 117 at the center of the target zone 146 allows the target zone to be treated continuously when the radiation beam 114 is created by the radiotherapy source 110 and is rotated by the ring mechanism 108.

Computer storage 160 is shown as containing image magnetic resonance data 170 that have been acquired by the magnetic resonance imaging module 106. The computer storage 160 is shown as further containing diagnostic images (i.e. image representation) 172 that have been reconstructed from the image magnetic resonance data. The computer storage 160 is shown as further containing coordinates 174 of the target volume 146. The computer storage 160 is shown as further containing radiotherapy control signals 178.

The computer memory 162 contains machine executable instructions 180, 182, 186, 188, 194 for operation by the processor 156. The computer memory 162 is shown as containing a therapy system control module 180. The therapy system control module 180 contains machine executable instructions which allow the processor 156 to control the overall functioning of the therapy system 100. The computer memory 162 is shown as further containing a radiotherapy apparatus control module 182. The radiotherapy apparatus control module 182 contains machine executable instructions which allow the processor 156 to control the functioning of the radiotherapy apparatus 102.

The computer memory 162 is shown as further containing a magnetic resonance imaging control module 186. The magnetic resonance imaging control module 186 contains machine executable code which allows the processor 156 to control the functioning and operation of the magnetic resonance imaging module 106. The computer memory 162 is shown as further containing an image reconstruction module 188. The image reconstruction module 188 contains machine executable code which is used by the processor 156 to transform the image magnetic resonance data 170 into images 172.

The computer memory 162 is shown as further containing radiotherapy control signal generation module 194. The radiotherapy control signal generation module 194 contains computer executable code which the processor 156 uses to generate the radiotherapy control signals 178. The radiotherapy control signals 178 may be generated in conjunction with the coordinates 174 of the target volume 146.

The computer memory 162 is shown as further comprising an algorithm 199. The algorithm 199 contains computer executable code which the processor 156 uses to detect discrepancies or anomalies in segmented MR images (and classified into tissues) by using reference images or reference data. For example, the algorithm 199 may be configured to compare the size of a bone segment or tissue in the segmented MR image with a reference diameter (of the reference data) that the bone tissue should not exceed. By identifying a discrepancy (e.g. the size exceeds the diameter) the algorithm 199 may request a modification of the segmented MR image.

In another example, since most structures of clinical interest have a known characteristic shape and anatomical location relative to other structures, the analysis of the segmented MR image using those characteristics may trigger the algorithm to request a modification of the segmented MR image. The analysis may be performed by for example aligning an MR image taken now with one taken on a previous occasion or aligning images of two objects that are expected a priori to be the same.

The computer memory 162 further contains computer-executable code which enables the processor 156 to execute at least part of the below described method.

Figure 2:
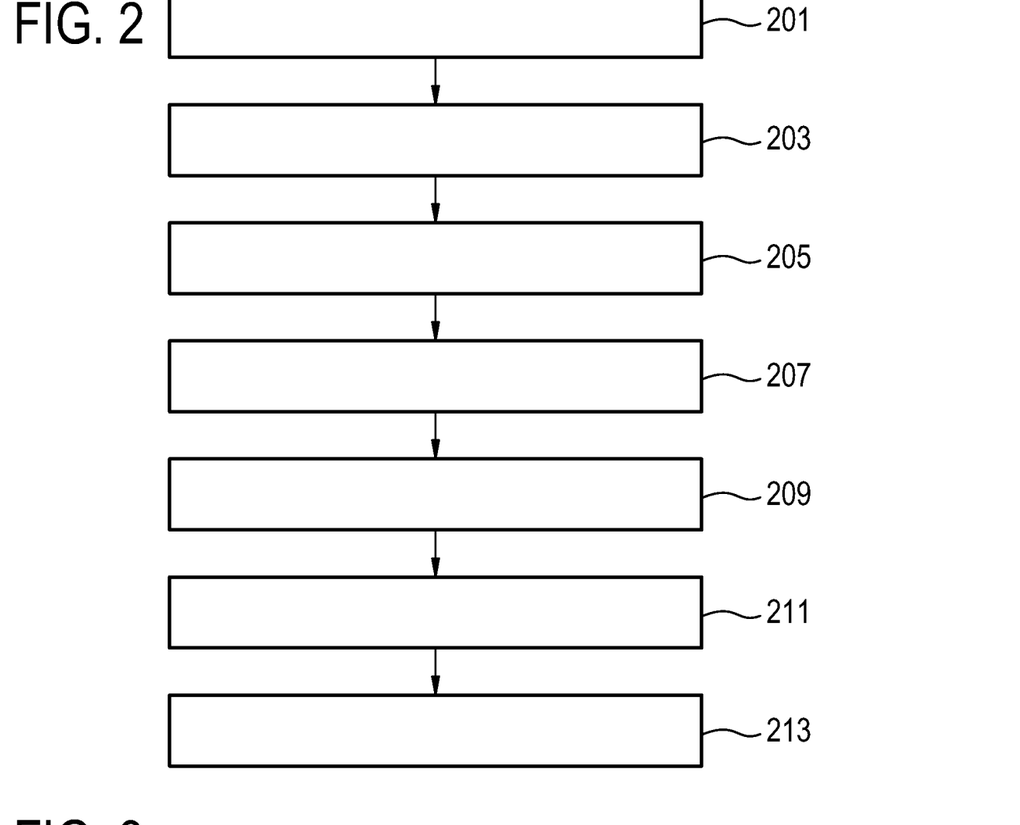
FIG. 2 is a flowchart of a method for controlling irradiation of an affected part of an organ.

FIG. 2 is a flowchart of a method of operating the therapy system 100 of FIG. 1 for controlling irradiation of an affected part of an organ 146 e.g. positioned in the examination volume 138. The organ may for example be a prostate. The organ may comprise a predefined marker. For example, one or more prostate pure gold fiducial markers of diameter 1.0 mm and length 3.0 mm may be inserted trans-rectally in the organ prior to performing step 201. The marker may comprise for example a metal object of a-priori known or predefined dimensions or an object that can have a-priori known or predefined contrast. For example, a user of therapy apparatus may also provide a predefined configuration of such shapes based on the type of the metal of the marker such as use a seed shape or barrel shape instead of a wire shape.

In step 201, magnetic resonance data may be acquired from the organ using the magnetic resonance imaging system e.g. 106. The acquired magnetic resonance data comprises 3D (three-dimensional) image data (e.g. by acquiring magnetic resonance data comprising 3D image data). The 3D image data may be acquired using a 3D acquisition or a 2D multislice acquisition. In one example, the acquired magnetic resonance data may further comprise 2D image data. Using two different sets of image data may be advantageous as it may avoid biases that may be caused by comparing data obtained in the same way. The acquisition of the 2D and/or 3D image data may be performed using a predefined pulse sequence. The pulse sequence may comprise for example a spin echo MRI pulse sequence or a T1-weighted gradient echo sequence.

In one example, the acquired magnetic resonance data may be segmented into a plurality of segments indicating respective tissues in the organ 146. A tissue may for example comprise a fat, water, bone or air tissue etc. For example, the segmenting may be performed by generating segments corresponding to bone, air and soft tissue (e.g., a water segment and a fat segment) by segmenting respective voxels. For example, the bone segment may comprise a first set of voxels of the 3D image data that indicate the bone tissue.

In one example, the segmenting may be performed by reconstructing an MR image using the acquired MR data, and segmenting the reconstructed MR image. The segmenting may comprise dividing up the reconstructed MR image into a patchwork of regions or segments each of which is homogenous e.g. in term of intensity and/or texture. The segmenting comprises the tissue classification. For example, the segmenting comprises assigning to each individual element of the reconstructed MR image a tissue class indicating the tissue into which belongs the individual element. The individual element may comprise a voxel. The tissue class may be assigned to the individual element by for example assigning a value e.g. number, specific to that tissue class. For example, each individual element of the MR image may be classified according to its probability of being a member or part of a particular tissue class. The segmentation may be advantageous for example when registering segmented MR data. E.g. the 2D and 3D image data may be segmented and segmented MR data may be registered. For the registration, raw image data or the segmented images may be transformed into new reference frames in which the geometric relationship between these structures is appropriate.

In an optional step 203, the image data of a reconstructed 2D image and the 3D image data may be registered or co-registered. The registration may be performed by for example aligning the two MRI image data, so that common features overlap and differences between the two image data are emphasized. The registration may find spatial or temporal correspondences between the 2D and 3D image data. The image registration may involve spatially registering the 2D image data to align with the 3D image data. Image registration may be intensity-based or feature-based. Intensity-based registration compares intensity patterns in images via correlation metrics, while feature-based registration finds correspondence between image features such as points, lines, and contours. In another example, the 2D image data and 3D image data may be used in the following steps without being registered.

In step 205, at least one signal void candidate of the marker may be identified in the reconstructed 2D image of the magnetic resonance data. For example, the 2D image may be reconstructed from the 3D image data or from the 2D image data. In another example, at least one signal void candidate may be identified for the organ being imaged if the organ has a predefined shape or structure that can be used (e.g. what is described herein for the marker may also be performed for other structures that are imaged using the MRI system 106, wherein the structures have predefined shapes or forms).

The signal void refers to a region in the reconstructed image emitting no radiofrequency signal e.g. because there are no activated protons in the region. The signal void identified in step 205 is a candidate as it may or may not be a signal void originated from or corresponding to the marker.

In one example, the identification may automatically be performed. For example, the signal void may be identified using magnetic resonance properties of pixels of the 2D image data. In another example, the signal void may randomly be selected as a given position of the reconstructed image.

In one example, the reconstructed 2D image may be displayed on a graphical user interface e.g. on display device 158. And, a selection may be received from a user of the therapy system 100. The selection indicates the identified signal void. The selection of the signal void may for example be performed by a movement (a drag action) of a cursor e.g. of the graphical user interface onto the position of the reconstructed 2D image that corresponds to the signal void.

In another example, the identification of the signal void comprises detecting by a sensor e.g. of the display device 158 a touch action on the (touch sensitive) display device 158 indicative of the signal void. The touch action may comprise a drag action. In another example, the touch action may be performed by orienting an entry pen of the display device 158 towards the signal void without contacting the display device 158.

In one example, multiple signal voids may be identified in step 205 e.g. so as to determine the shape of the marker. This may be done either by repeating step 205 multiple times or by identifying at once the multiple signal voids. The identification of the multiple signal voids may be performed as described above.

In step 207, the 3D image data and the identified signal void may be processed for calculating a likelihood that the identified signal void candidate is part of the marker. In other words, it is a likelihood that the signal or no signal in the signal void is originated from marker. The identified signal void candidate is part of the marker means that the signal void is originated or caused by the presence of the marker in the imaged part of the organ.

The likelihood determination that the signal void is part of the marker may be a binary determination (e.g. part of the marker or not part of the marker) but it is also contemplated that other determinations, such as values representing a probability that the signal void is part of the marker, can be employed.

The likelihood or probability may be calculated for each signal void identified in step 205. The calculation of the likelihood may for example use both the image intensity information and morphological information, such as the position of the pixels of the signal void. For example, a probability density function correlating the pixels of the signal void with image intensity data in the 3D image data, may be used in a Bayesian schema to generate the likelihood estimates for each identified signal void.

In one example, the processing of the 3D image data in step 207 may comprise identifying pixels in the 2D image data corresponding to the identified signal void, comparing magnetic resonance properties of the pixels with magnetic resonance properties of voxels of the 3D image data; and calculating the likelihood using the comparison result.

In another example, the processing of the 3D image data in step 207 may comprise providing reference values of one or more parameters describing the shape of the marker; processing the 3D image data for determining the shape of the marker using magnetic resonance properties of the signal void; determining values of the parameters using the determined shape of the marker; comparing the determined values with the reference values; and calculating the likelihood using the comparison result. The determined shape of the marker may for example be confirmed by using a distribution on log-intensities of voxels containing the marker, and that distribution may be checked if it is a Gaussian around a predefined mean intensity value.

In a further example, the processing of step 207 may comprise dragging the shape of the marker on top of the area where the signal void likely is and using the length (and volume) information to limit the algorithmic search to the likely nearby image elements in the 3D volume (e.g. voxels). Because the wire may deform (but not shrink or expand) the present method may use this information in deducing the likely location of the signal void.

For example, the reconstructed 2D image may be displayed as a probability map (color-coding, etc) for the likelihood of finding the marker at the identified signal void.

In step 209, an indication of the calculated likelihood(s) may be provided or output. For example, the outputting comprises displaying an indication of the likelihood in association with the 2D image as shown with reference to FIG. 3 e.g. using visual cues. In response to the outputting of the calculated likelihoods or in response to providing the calculated likelihoods, a user input may be received in step 211 specifying a radiation therapy (or a radiation therapy plan). The user input may specify for example 3D contour regions, direction and/or placement of the radiation for a radiation therapy plan for controlling the irradiation of the affected part of the organ.

In step 213, the irradiation of the organ may be controlled using the radiation therapy (or using the radiation therapy plan). The radiation therapy refers to the treatment of a specific tissue (e.g. the organ), for example a tumorous tissue of the organ, using applied high-energy radiation e.g. at a predefined position. By providing the likelihoods as described above, the direction and placement of the radiation may be accurately controlled. This may ensure both that the treatment volume or tumor or the affected part receives a desired or sufficient amount of radiation in order to be treated or destroyed and that damage or negative effects to the surrounding healthy or non-tumorous tissue may be avoided or minimized.

In one example, the steps 205-207 of identifying the signal voids and determining their corresponding likelihoods may be repeated and in each iteration the shape of the marker may be determined as described above. In case, the shape of the marker changes with respect to the shape of the marker from the previous iteration steps 209-213 of outputting, receiving and controlling the apparatus may be performed; otherwise steps 205-207 may be repeated and so on.

Figure 3:
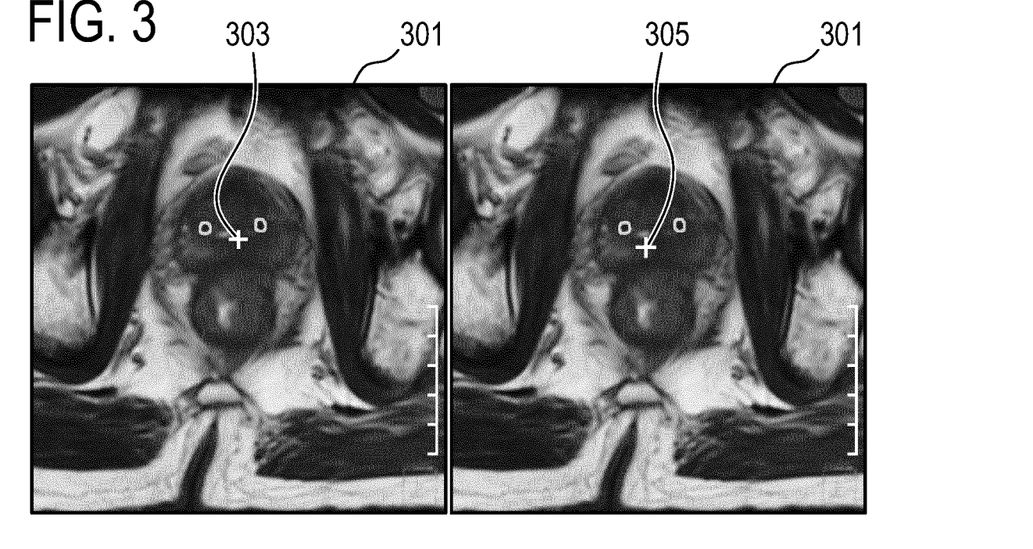
FIG. 3 shows an example of 2D MR image with signal voids.

FIG. 3 shows an example of reconstructed 2D MRI image of a prostate. The prostate comprises a marker such as a metal wire or gold seed.

First, a user may select the signal void to be tracked. For example the signal void may be caused by the gold. Then the user may have access to 2D images 301 that show the prostate area. The user may then moves the mouse over potential black signal voids on the 2D image 301 as illustrated by the crosses 303 and 305. When the mouse pointer moves or hovers over the 2D image, the underlying algorithm or software is triggered to calculate the model fit to the current pointer location 303-305. The model fit value can then be normalized to three categories: no-fit, possible-fit and good-fit. The categorization may be reflected on the user interface by changing the pointer 303-305 color accordingly, for example, white for no-fit, yellow for possible-fit, and green for good-fit. no-fit, possible-fit and good-fit may indicate the likelihood that the signal void identified or selected by the pointers 303-305 is part of the marker or not part of the marker. For example, no-fit may indicate that identified signal void is not part of the marker.

In another example, the signal voids may automatically be generated or identified on the 2D image 301 and regions (e.g., pixels) of the 2D image that correspond to the signal void are assigned a value that corresponds to the goodness of the fit when the given region is the center of the model to be fitted. This value can then be turned into color-coded overlay that shows at a glance where the models fit well.

In one example, the present disclosure provides user interface cues on underlying 3D structures when the user interacts with a representative 2D medical image slice. The user interface can indicate that the signal void on the image is actually interconnected on adjacent slices and forms a candidate for a metal wire marker. Because the MR image resolution can be poor in comparison with marker dimensions, or the image can be noisy or lacking contrast, the user interface can include the quality of fit to the visual cue, so that the user can provide several signal void candidates in rapid succession and quickly see what the most likely cases of the wire are. The present method may also be used for other applications where the user needs to label or contour organs or structures with a-priori known model.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 therapy system
102 radiotherapy apparatus
104 mechanical actuator
106 magnetic resonance imaging module
108 ring mechanism
110 radio therapy source
112 multi-leaf beam collimator
114 radiation beam
116 rotational axis
117 rotational point
122 main magnet
124 cryostat
126 superconducting coil
128 compensation coil
130 low magnetic field zone
132 magnet axis
134 magnetic field gradient coil
136 magnetic field gradient coil power supply
138 imaging volume
140 radio frequency coil
142 radio frequency transceiver
144 subject
146 target volume
148 patient carrier
150 mechanical positioning system
152 computer system
154 hardware interface
156 processor
158 user interface
160 computer storage
162 computer memory 164 top distance
166 bottom distance
170 image magnet resonance data
172 diagnostic images
174 coordinates of target volume
178 radio therapy control signals
180 therapeutic apparatus control module
182 radio therapy apparatus control module
186 magnetic resonance imaging control module
188 image reconstruction module
194 radio therapy control signal generation module
199 program
201-213 steps
301 2D image
303-305 pointer.

The invention claimed is:

1. A system, comprising:
a magnetic resonance imaging apparatus;
a radiotherapy apparatus;
a processor for controlling the system; and
a memory containing machine executable instructions, wherein execution of the machine executable instructions causes the processor to:
  cause the magnetic resonance imaging apparatus to acquire magnetic resonance data from an organ which is marked by a marker, wherein the magnetic resonance data comprises three dimensional (3D) image data, or 3D image data and two dimensional (2D) image data;
  provide reference values of one or more parameters describing the shape of the marker;
  identify in a reconstructed 2D image reconstructed from the 3D image data or from the 2D image data at least one signal void candidate of the marker, or receive a user input with respect of an identification of the signal void candidate of the marker in the reconstructed 2D image reconstructed from the 3D image data or from the 2D image;
  process the 3D image data for determining the shape of the marker using magnetic resonance properties of the signal void candidate;
  determine values of the parameters using the determined shape of the marker;
  compare the determined values with the reference values;
  calculate a likelihood that the identified signal void candidate is part of the marker using the comparison result;
  output to a user an indication of the calculated likelihood;
  in response to the outputting of the calculated likelihood, receive a user input with respect to a radiation therapy plan; and
  control the radiotherapy apparatus to irradiate the organ in accordance with the radiation therapy plan.

2. The system of claim 1, wherein execution of the instructions further causes the processor to automatically identify the signal void candidate using magnetic resonance properties of pixels of the 2D image.

3. The system of claim 1, wherein execution of the instructions further causes the processor to display on a graphical user interface the 2D image and to receive a selection of the identified signal void candidate.

4. The system of claim 1, wherein the outputting comprises displaying an indication of the likelihood in association with the 2D image.

5. The system of claim 1, wherein execution of the instructions further causes the processor to repeat the identifying and the processing steps for delineating the shape of the marker on the 2D image.

6. The system of claim 1, wherein the at least one signal void candidate comprises a plurality of signal void candidates, wherein the processing of the 3D image data and each identified signal void candidate of the plurality of signal voids is performed for calculating a likelihood that each of the identified signal void candidates is part of the marker; wherein execution of the instructions further causes the processor to build a shape of the marker using the likelihood that each of the identified signal void candidates is part of the marker.

7. The system of claim 6, wherein the parameters are shape independent parameters.

8. The system of claim 6, wherein the parameters comprise the volume and size of the marker.

9. The system of claim 6, wherein the magnetic resonance properties comprise at least one of intensity or magnitude of the signal.

10. The system of claim 1, wherein the organ is a prostate and the marker is an object having a predefined shape and/or predefined contrast.

11. The system of claim 1, wherein the radiotherapy apparatus comprises a radiotherapy source for producing a radiation beam, and a beam collimator for collimating the radiation beam.

12. The system of claim 11, wherein the radiotherapy apparatus further comprises a ring mechanism, wherein the ring mechanism is configured to rotate the radiotherapy source and the beam collimator about a rotational point of the radiotherapy apparatus.

13. A computer program product comprising machine executable instructions stored on a non-transitory computer readable medium for execution by a processor controlling a system, wherein execution of the machine executable instructions causes the processor to:
  receive magnetic resonance data, the magnetic resonance data comprising three dimensional (3D) image data, or 3D image data and two dimensional (2D) image data, that are acquired using a magnetic resonance imaging apparatus from an organ, wherein the organ is marked by a marker;
  provide reference values of one or more parameters describing the shape of the marker;
  identify in a reconstructed 2D image reconstructed from the 3D image data or from the 2D image data at least one signal void candidate of the marker;
  process the 3D image data and the identified signal void for determining the shape of the marker using magnetic resonance properties of the signal void candidate;
  determine values of the parameters using the determined shape of the marker;
  compare the determined values with the reference values;
  calculate a likelihood that the identified signal void candidate is part of the marker using the comparison result;
  output to a user an indication of the calculated likelihood;
  in response to the outputting, receive a user input with respect to a radiation therapy plan; and
  control a radiotherapy apparatus to irradiate the organ using the radiation therapy plan.

14. The computer program product of claim 13, wherein the radiotherapy apparatus comprises a radiotherapy source for producing a radiation beam, a beam collimator for collimating the radiation beam, and a ring mechanism, wherein the ring mechanism is configured to rotate the radiotherapy source and the beam collimator about a rotational point of the radiotherapy apparatus, and wherein controlling the radiotherapy apparatus comprises controlling the beam collimator and the ring mechanism to cause the radiotherapy apparatus to irradiate the organ in accordance with the radiation therapy plan.

15. The computer program product of claim 13, wherein execution of the machine executable instructions further causes the processor to display on a graphical user interface the 2D image and to receive from the user a selection of the identified signal void candidate.

16. The computer program product of claim 13, wherein the outputting comprises displaying an indication of the likelihood in association with the 2D image.

17. A method, comprising:
using a magnetic resonance imaging system to acquire magnetic resonance data from an organ, wherein the organ is marked by a marker, wherein the magnetic resonance data comprises three dimensional (3D) image data, or 3D image data and two dimensional (2D) image data;
identifying, in a reconstructed 2D image reconstructed from the 3D image data or from the 2D image data, data at least one signal void candidate of the marker;
providing reference values of one or more parameters describing the shape of the marker;
processing the 3D image data and the identified signal void for determining the shape of the marker using magnetic resonance properties of the signal void candidate;
determining values of the parameters using the determined shape of the marker;
comparing the determined values with the reference values;
calculating a likelihood that the identified signal void candidate is part of the marker using the comparison result;
outputting to a user an indication of the calculated likelihood;
in response to the outputting of the calculated likelihood, receiving a user input with respect to a radiation therapy plan; and
controlling a radiotherapy apparatus to irradiate the organ in accordance with the radiation therapy plan.

18. The method of claim 17, wherein the radiotherapy apparatus comprises a radiotherapy source for producing a radiation beam, a beam collimator for collimating the radiation beam, and a ring mechanism, wherein the ring mechanism is configured to rotate the radiotherapy source and the beam collimator about a rotational point of the radiotherapy apparatus, and wherein controlling the radiotherapy apparatus comprises controlling the beam collimator and the ring mechanism to cause the radiotherapy apparatus to irradiate the organ in accordance with the radiation therapy plan.

19. The method of claim 17, further comprising displaying on a graphical user interface the 2D image, and receiving from the user a selection of the identified signal void candidate.

20. The method of claim 17, wherein the outputting comprises displaying an indication of the likelihood in association with the 2D image.

* * * * *